United States Patent [19]

Kline

[11] Patent Number: 5,804,188
[45] Date of Patent: Sep. 8, 1998

[54] METHOD AND COMPOSITION FOR TREATMENT OF DISORDERS INVOLVING IMMUNOLOGICAL DYSFUNCTION

[75] Inventor: Ellis L. Kline, Pendleton, S.C.

[73] Assignee: Molecular Rx, Inc., Pendleton, S.C.

[21] Appl. No.: 413,921

[22] Filed: Mar. 29, 1995

Related U.S. Application Data

[63] Continuation of Ser. No. 46,611, Apr. 19, 1993, abandoned, which is a continuation-in-part of Ser. No. 871,968, Apr. 22, 1992, abandoned.

[51] Int. Cl.$^6$ ........................ A61K 39/00; A61K 39/395; A61K 38/00; G01N 33/564
[52] U.S. Cl. ..................... 424/184.1; 424/146.1; 424/94.6; 514/2; 514/825; 435/194; 436/506; 436/507; 436/508; 436/509; 536/1.1
[58] Field of Search .............................. 424/184.1, 146.1, 424/94.6; 514/825, 2; 435/194; 436/506, 507, 508, 509; 536/1.1

[56] References Cited

U.S. PATENT DOCUMENTS 4,294,818  10/1981  McMichael et al. .
5,077,211  12/1991  Yarosh .
5,116,615   5/1992  Gokcen et al. .

OTHER PUBLICATIONS

Kotzin, B.L. et al., "Preferential T–cell Receptor β–chain Variable Gene Use in Myelin Basic Protein–reactive T–cell Clones from Patients with Multiple Sclerosis," *PNAS*, vol. 88, pp. 9161–9165 (Oct. 1991).

McNeilage, L.J. et al., "Review: Autoantibodies Reactive with Small Ribonucleoprotein Antigens: A Convergence of Molecular Biology Clinical Immunology," *J. Clin. Lab. Immunol.*, vol. 15, pp. 1–17, (1984).

Stetler et al., "Antibodies to Distinct Polypeptides of RNA Polymerase I in Sera From Patients with Rheumatic Autoimmune Disease," *PNAS*, vol. 79, pp. 7499–7503 (Dec. 1982).

Stetler et al., "Immunization of Rabbits with Purified RNA Polymerase I Induces A Distinct Population of Antibodies Against Nucleic Acids As Well As Anti–RNA Polymerase I Antibodies Both Characteristic of Systematic Lupus Erythematosus," *PNAS*, vol. 82, pp. 6797–6801 (Oct. 1985).

Reimer et al., "Autoantibody to RNA Polymerase I in Scleroderma Sera," *J. Clin. Invest.*, vol. 79, pp. 65–72 (Jan. 1987).

*Biochemical and Organic Compounds for Research and Diagnostic Clinical Reagents Catalog*, Sigma Chemical Co., p. 1266 (1988).

*Primary Examiner*—Nita Minnifield
*Attorney, Agent, or Firm*—Jones & Askew, LLP

[57] ABSTRACT

A method and composition are provided for treatment of disorders involving immunological dysfunction. The invention comprises the administration of a low level of ribonucleotide polymerase protein or a derivative thereof to a human or animal with an immune dysfunction disorder.

20 Claims, 3 Drawing Sheets

METHOD AND COMPOSITION FOR TREATMENT OF DISORDERS INVOLVING IMMUNOLOGICAL DYSFUNCTION

CROSS-REFERENCE TO RELATED APPLICATIONS

This is a continuation of application Ser. No. 08/046,611 filed Apr. 19, 1993 now abandoned, which is a continuation-in-part of application Ser. No. 07/871,968 filed Apr. 22, 1992 now abandoned.

FIELD OF THE INVENTION

The present invention is related to a method and composition for the treatment of a variety of disorders involving immunological dysfunctions. More particularly, the present invention relates to the treatment of certain immunological disorders comprising the step of administering ribonucleotide polymerase, or a compound related to ribonucleotide polymerase, at very low concentrations to a human or animal with an immunological dysfunction. In certain situations, synergists, such as glycerin, glutamine or other synergists, can be administered with the ribonucleotide polymerase to enhance therapeutic activity.

BACKGROUND OF THE INVENTION

The abnormal functioning of the cell-mediated and/or humoral immune response in animals or humans can result in the manifestation of disorders which are not anaphylactic in nature, but result in abnormal targeting of certain disease tissues. Disorders involving immunological dysfunction cause a wide variety of symptoms. Examples of immunodeficiency disorders are diseases which mask immune targeting, such as various malignancies, herpes related disorders, Acquired Immune Deficiency Syndrome (HIV infections), and diseases in which the host itself manufactures self-destructive substances including, but not limited to, systemic lupus erythematosus, arthritis, diabetes, thyroiditis, hemolytic anemia, atrophy orchitis, Goodpasture's disease, autoimmune retinopathy, autoimmune thrombocytopenia, sympathetic opthalmia, myasthenia gravis, Grave's disease, primary biliary cirrhosis, chronic aggressive hepatitis, ulcerative colitis, membrane glomerulophathy, dermatitis, laminitis, chronic glomerulonephritis, Sjögren's syndrome, Reiter's syndrome, myositis, systemic sclerosis, polyarteritis and multiple sclerosis.

In prior years it was believed that an anti-self response was harmful and that such responses did not occur normally. More recently, it has become apparent that normal immune responses involve self-self recognition. Moreover, many individuals produce nonpathogenic antibodies reactive with self-antigens. As a result, our present understanding is that disease occurs only when anti-self reactions are either excessive or productive of especially injurious immune responses.

A disease state resulting from the abnormal targeting of the humoral or cell-mediated response to immunogens (either external or internal) is manifested by a hypersensitivity response. Such a response is usually classified as one of four types:

Type I: Anaphylactic reactions. These reactions are mediated by IgE antibodies which bind to receptors on mast cells. When cross-linking occurs with antigens, the IgE antibodies stimulate the mast cells to release a number of pharmacologically active substances that can cause the symptoms characteristic of anaphylaxis. These reactions to antigenic challenge are immediate and potentially life-threatening. Examples of Type I response include, but are not limited to, allergic rhinitis, gastrointestinal allergy, atopic dermatitis, bronchial asthma and equine heaves, and laminitis. An autoimmune disorder that involves an anaphylactic reaction is "milk allergy" in cattle.

Type II: Cytotoxic (cytolytic) reactions. These cell surface reactions result from an interaction of antigen with IgM and/or IgG which activates the complement cascade, leading to the destruction of the cell. Examples of Type II reactions include, but are not limited to, leukocytopenia, hemolytic disease of newborn and Goodpasture's disease. Autoimmune disorders that involve cytotoxic/cytolytic reactions are hemolytic anemia, thrombocytopenia and thyroiditis.

Type III: Immune complex reactions. Type III reactions occur when large complexes of antigen and IgG or IgM accumulate in the circulation or in tissue, fixing complement. Granulocytes are attracted to the site of complement fixation and release damaging lytic enzymes from their granules. An example of this type of reaction is serum sickness. Autoimmune disorders that involve Type III reactions include systemic lupus erythrematosus, chronic glomerulonephritis and rheumatoid arthritis.

Type IV: Cell-mediated immunity (CMI) reaction, or delayed-type hypersensitivity (DTH). In contrast to the first three types of immune responses, this hypersensitivity response is mediated by T cells rather than antibodies. Activated T cells release lymphokines which can result in the accumulation and activation of macrophages, K cells and NK cells, which cause local tissue damage. This reaction can occur 1–2 days after antigenic challenge. Examples of Type IV reactions include, but are not limited to, contact dermatitis, tuberculosis, allergic encephalitis, thyroiditis and primary homograft rejection. The autoimmune disorder juvenile diabetes mellitus may involve this type of reaction.

Under normal circumstances, all of the above types of reactions provide the individual with protection from disease. Hypersensitivity reactions, though operating through the same basic cellular and molecular mechanisms, represent an exaggerated or inappropriate response which damages the host. Thus, many of the disease manifestations outlined above are referred to as anti-self disorders, or "autoimmune" diseases.

Recently, it has become apparent that normal immune responses do involve self-self recognition. These recognitions are the result of immune cells reacting with self antigens in a non-pathogenic manner. A disease state occurs when anti-self reactions are either excessive or produce especially injurious immune responses. For example, it is currently believed that many autoreactive clones of T and B cells exist in the normal state but are regulated by homeostatic mechanisms. It is the breakdown of these control mechanisms that leads to the activation of the autoreactive clones and autoimmune disease.

Although B lymphocytes and their progeny are responsible for antibody production, under most circumstances they require helper T lymphocyte function for activation and differentiation into antibody-secreting cells. Moreover, helper T cells and their derivative products appear capable of down-regulating immune responses. If the T cell population is self-tolerant, it may prevent B cells capable of differentiating into auto-antibody-producing cells from proliferating and differentiating. A defect in self-tolerance mechanisms could occur at any of several steps in the immune pathway. Individuals with B cells capable of producing pathogenic auto-antibodies which have been heretofore held in check by T cells may, under such circumstances, be driven to produce large amounts of injurious antibodies. Because it is the quantity of autoantibody that determines whether or not disease occurs, quantitation aspects of immune regulation and immune stimulation may be critical to the balance between disease development versus relative health with minor immune abnormalities.

In addition, strong immune stimulation can overwhelm normal regulatory mechanisms and drive B cells to produce antibodies and autoantibodies without the usual requirements for, or regulation by, T cells. Examples of such stimuli include graft-versus-host disease (as after allogenic bone marrow transplantation) or stimulation by any of a variety of powerful polyclonal immune activators (endotoxin) or even viruses which stimulate B cells (Epstein-Barr virus). Curiously, these same antigens may also prove therapeutic. Enterotoxin has been shown to reduce the severity of autoimmune lupus nephritis in mice and has protected animals from experimental allergic encephylomyelitis. Just a few hundred molecules of a substance, a toxin, for instance, can trigger immune cell communication and replication.

One example of an autoimmune state where anti-self reactions are excessive, as described above, is systemic lupus erythematosus (SLE). This disease, of unknown etiology, is characterized by a variety of self antigens, including nuclear, cytoplasmic and cell membrane antigenic determinants. There is no one clinical or laboratory abnormality which is pathognomonic for the disease. Although anti-DNA antibodies occur in approximately 70% of patients with SLE, individual patients show marked variability in their clinical symptomology and laboratory findings. As a result, criteria have been developed and modified in an attempt to included patients with systemic lupus erythematosus and to exclude patients with other disorders including, but not limited to, rheumatoid arthritis, progressive systemic sclerosis, polymyositis and Sjögren's syndrome.

Tremendous variability exists in the clinical signs and symptoms manifested by different patients. In some, periods of heightened disease activity alternate with months or years of reduced disease activity. Such variability demands an individualized approach to prognosis and therapy. Whereas some patients with systemic lupus erythematosus have large amounts of antiDNA and positive LE cell tests, others do not. At one end of the clinical spectrum are patients with mild illness characterized perhaps by fatigue, arthralgias, sun sensitivity, rash, and antinuclear antibodies. At the other end of the spectrum are individuals who manifest rapidly progressive renal inflammatory disease or severe CNS dysfunction. Most fall between the mildest form who require little or no treatment and those with severe major organ involvement who require intensive therapy. In addition to spontaneous idiopathic systemic lupus erythematosus, the disease may be induced in humans by certain drugs. Many other animals, i.e., dogs, cats, mink, horses and mice, develop a systemic lupus erythematosus-like syndrome.

Arthritis, in particular rheumatoid arthritis, is another inflammatory autoimmune disorder. It is a common assumption that genetics and environmental factors determine the course of the disease. It typically begins as pain, tenderness, and swelling of one or more joints in the extremities. Classically, the involvement is symmetrical, but is commonly more severe on the dominant side. The small joints of the hands and feet, particularly the proximal interphalangeal, metatarsophalangeal, and metacarpophalangeal joints are involved, although involvement of wrists, ankles, knees, elbows, and hips is also common. Patients positive for rheumatoid factor and antinuclear antibodies at the initiation of their disease also have greater likelihood of running an adverse disease course. Skin ulceration is the most common extrareticular manifestation. High titered positive tests for rheumatoid factors, presence of circulating immune complexes, and mildly depressed complement titers are characteristic of patients with systemic manifestation. Spavin, in the hock of horses, is of similar etiology.

To date, there is no satisfactory treatment of most diseases caused by immune dysfunction. What is needed is a method and composition which is effective in alleviating the symptoms of these diseases without causing other side effects. The method should be safe and effective in treating symptoms associated with a wide variety of these diseases.

SUMMARY OF THE INVENTION

The present invention provides a method and composition for alleviating the symptoms of disease states associated with immunodeficiencies and abnormal humoral and cellular related immune disorders. The present invention comprises administration to the human or animal with the immunologic dysfunction, an effective dose of a ribonucleotide polymerase or a fraction or derivative thereof. The preferred ribonucleotide polymerase is RNA polymerase. The effective dose is extremely low and does not cause side effects, such as an anaphylactic response to the ribonucleotide polymerase. In addition, the dose of RNA polymerase that is administered to the human or animal generally will not elicit an antibody response.

It has been found that the administration of extremely low amounts of ribonucleotide polymerase to a human or animal with an immune dysfunction causes the mitigation or elimination of the symptoms of the immune dysfunction. The ribonucleotide polymerase can be administered in combination with synergists to enhance its therapeutic effect. Examples of these synergists include, but are not limited to, glycerin, glutamine, histamine and neuraminidase.

Accordingly, it is an object of the present invention to provide a method and composition for treating disorders involving Immunological dysfunction.

It is yet another object of the present invention to provide a method and composition for the treatment of systemic lupus erythematosus.

It is yet another object of the present invention to provide a method and composition for the treatment of laminitis.

It is yet another object of the present invention to provide a method and composition for the treatment of dermatitis.

It is yet another object of the present invention to provide a method and composition for the treatment of arthritis.

It is yet another object of the present invention to provide a method and composition for the treatment of autoimmune retinopathy disorders such as Voyt-Aoyanagi-Harada syndrome.

It is yet another object of the present invention to provide a method and composition for the treatment of malignancies.

It is yet another object of the present invention to treat certain infectious diseases such as AIDS.

These and other objects, features, and advantages will become apparent after a review of the following detailed description of the disclosed embodiments and the appended claims.

DETAILED DESCRIPTION

As used herein, the term "ribonucleotide polymerase" means any protein that has ribonucleotide polymerase activity or has an amino acid sequence that is substantially similar to a protein which has ribonucleotide polymerase activity. The ribonucleotide polymerase includes, but is not limited to, ribonucleic acid (RNA polymerase) polymerase and reverse transcriptase. The ribonucleotide polymerase that can be used to practice the present invention can also be an inactivated enzyme or part of the enzyme.

The term "immunological dysfunction" includes, but is not limited to, any immunodeficiency disorder characterized by failure of the immune system and its associated systems to mount an immune response, and/or humoral and cell mediated injury as a result of external or internal immunogen substances. The term also includes aberrant immune responses such as those observed in autoimmune diseases.

The term "therapeutically effective amount of ribonucleotide polymerase" as used herein means an amount of ribonucleotide polymerase sufficient to mitigate or eliminate the symptoms of an immunological dysfunction disorder. Representative preferred doses and concentrations are disclosed herein. The term "synergist", as used herein, means any compound or composition that will enhance the therapeutic effect of the RNA polymerase.

The present invention provides a method and composition for alleviating the symptoms of disease states associated with immune dysfunction. The present invention comprises administration to the human or animal with the immune dysfunction an effective dose of ribonucleotide polymerase or a fraction or derivative thereof. The effective dose is extremely low and does not cause an anaphylactic response to the ribonucleotide polymerase-type protein.

In practice, the present invention comprises the administration of less than approximately $10^{-2}$ mg per dosage unit of ribonucleotide polymerase to a human or animal with an immune dysfunction. A preferred dose of ribonucleotide polymerase or active derivative thereof is between approximately $10^{-2}$ mg to $10^{-8}$ mg. A more preferred dose of ribonucleotide polymerase is between approximately $10^{-3}$ mg and $10^{-7}$ mg. The most preferred dose of ribonucleotide polymerase is approximately $10^{-4}$ mg. Preferably, the total periodic daily dosage does not exceed about $10^{-2}$ mg per subject, and still more preferably does not exceed from about $5 \times 10^{-3}$ to $10^{-4}$ mg. Thus, the present invention encompasses a composition comprising a solution of ribonucleotide polymerase or an active derivative thereof that is present in the solution at a concentration of between approximately $10^{-3}$ to $10^{-7}$ mg.

Because there may be a significant variation in specific activity of RNA polymerase from lot to lot and from manufacturer to manufacturer, depending upon such factors as source of the enzyme, method of purification and other factors, it is preferred that the dose of RNA polymerase be expressed as "units of activity." The definition of a unit of activity for RNA polymerase varies depending on the source of the RNA polymerase. The term "unit" is defined by the individual manufacturers. Definitions quoted from several manufacturers, and including reverse transcriptase, are provided below:

A. RNA polymerase from *E. coli* K-12 (Sigma Chemical Company): "One unit will release 1.0 nanomole ($10^{-9}$ mole) of PP, in 10 minutes at pH 7.9 at 37° C. using calf thymus DNA as template."

B. $T_3$ RNA polymerase (RNA polymerase from bacteriophage $T_3$, Pharmacia Biotech, Inc.): "One unit catalyzes the incorporation of 1 nmole of AMP into acid-insoluble product in 50 µl of assay buffer in 60 minutes at 37° C., using a plasmid containing a $T_3$ promoter."

C. AMV reverse transcriptase, (Promega Corporation): "One unit is defined as the amount of enzyme required to catalyze the incorporation of 1 nmol of dTTP into acid insoluble form in 10 minutes at 37° C. in 0.05M Tris-HCl, pH 8.3, 40 mM KCl, 7 mM MgCl$_2$, 10 mM DTT, 0.1 mg/ml BSA, 0.5 mM 3H-dTTP, and 130 µg/ml rA$_{400}$: dT$_{50}$, 10:1."

D. M-MLV reverse transcriptase, RNase H Minus (Promega Corporation): "One unit is the amount of enzyme which incorporates 1 nmole of dTTP into acid insoluble form in 10 minutes at 37° C. in 50 mM Tris-HCl, pH 8.3, 40 mM KCl, 10 mM DTT, 7 mM MgCl$_2$, 0.1 mg/ml BSA, 0.5 mM $^3$H-dTTP and 130 µg/ml rA$_{400}$: dT$_{50}$, 10:1." (Note: This is the same definition as for C., but is worded differently in the catalog.)

Promega Corporation, which supplies reverse transcriptase, does not provide information about the amount of protein in a given lot of reverse transcriptase, therefore specific activity cannot be accurately calculated. Promega provides units/ml, which is typically 20,000–25,000 units per ml for AMV reverse transcriptase and 100,000–200,000 units per ml for M-MLV reverse transcriptase. For our calculation purposes we are assuming a protein concentration of a 1 mg/ml. Therefore, the specific activity of reverse transcriptase is very different from that of RNA polymerase.

Also, the two sources of RNA polymerase vary considerably in their specific activities. RNA polymerase from *E. coli* K-12 has a specific activity range of 1000–5000 units/mg; $T_3$ RNA polymerase has a specific activity range of 200,000–400,000 units/mg. These differences were taken into account in the protein range calculations of the present invention.

Thus, in practicing the present invention, one can measure the specific activity of the RNA polymerase and then use the amount of enzyme that has a total activity of between 0.0004 units and 4000 units which corresponds to a protein range of between approximately $1 \times 10^{-9}$ to 4.0 mg. The preferred range of RNA polymerase activity is between 0.04 to 100 units with the most preferred range of between 0.1 and 10 units of activity.

In a second aspect of the invention there is provided a pharmaceutical composition comprising a vehicle for the administration of ribonucleotide polymerase, or a fraction or derivative thereof, which comprises an amount of up to about $10^{-2}$ mg ribonucleotide polymerase, or fraction or derivative thereof, and pharmaceutically inert ingredients. In a preferred aspect, the pharmaceutical composition has an amount of between approximately $10^{-2}$ to about $10^{-8}$ mg ribonucleotide polymerase or fraction or derivative thereof. The preferred volume in which the RNA polymerase is present is between approximately 0.05 ml and 0.5 ml. However, other dose volumes are acceptable in practicing the present invention.

The present invention comprises the administration of an amount not to exceed approximately $10^{-2}$ mg per 24 hour period, although, in certain cases, the total amount of ribonucleotide polymerase administered in any one day may exceed the preferred limit. The ribonucleotide polymerase can be administered as a liquid or it can be administered as a solid wherein the ribonucleotide polymerase is embedded or admixed in a biodegradable or bioerodible matrix. The matrix can be a time release matrix. These matrices are well known to those of ordinary skill in the art and are not critical to the present invention. The ribonucleotide polymerase can be administered by subcutaneous injection or by sublingual route. The RNA polymerase can also be administered via intramuscular injection, intraperitoneal injection or intravenous injection. The RNA polymerase can also be administered transdermally or through mucosal membranes. The preferred route of administration of the RNA polymerase is by subcutaneous injection or by sublingual route.

In another embodiment, the ribonucleotide polymerase can be administered with other compounds to enhance its therapeutic effect. An example of ribonucleotide polymerase being used in combination with other immune system affecting molecules (synergists) include, but are not limited to, glycerin at a dose of between approximately $5 \times 10^{-1}$ mg to $2 \times 10^{-8}$ mg per dose, glutamine at a dose of between approximately $2.2 \times 10^{-2}$ mg to $2 \times 10^{-8}$ mg per dose, neuraminidase at a dose of between approximately $10^{-2}$ mg to $10^{-8}$ mg, or histamine at a dose of between approximately $10^{-2}$ mg to $10^{-8}$ mg.

In one embodiment, the vehicle is an aqueous solution that is contained within an inert container. In another variation, the composition is in the form of a suppository. The liquid form of the composition is preferably injected subcutaneously, although other routes of injection are contemplated as part of the present invention. In addition, the composition can be administered through the mucosal membranes, such as nasal membranes. The liquid carrier includes, but is not limited to, 0.1% phenol in saline (0.9% NaCl). Other pharmaceutically acceptable carriers can be used to administer the ribonucleotide polymerase.

The ribonucleotide polymerases that can be used in practicing the present invention include, but are not limited to, RNA polymerase (Nucleoside triphosphate: RNA nucleotydyltransferase [DNA-directed]; EC2.7.7.6), and reverse transcriptase (RNA-directed DNA polymerase, DNA nucleotydyl transferase [RNA-directed], revertase, EC 2.7.7.49). It is to be noted that the ribonucleotide polymerase can be either enzymatically active or enzymatically inactive. In addition, proteins with substantially similar amino acid sequences as the native enzymes can be used in practicing the present invention. It is also contemplated as part of the present invention that the ribonucleotide polymerase can be administered as a mixture of different ribonucleotide polymerases. It is to be understood that the source of ribonucleic acid polymerase is not critical to the present invention. For example, RNA polymerase from *E. coli* and from the bacteriophage T3 are both effective in carrying out the present invention.

The ribonucleotide polymerase can be administered by standard methods, including, but not limited to, intramuscular and subcutaneous routes. The ribonucleotide polymerase can also be administered by sublingual and intranasal routes. Because the effective amount of ribonucleotide polymerase in a dose is low, the composition according to the present invention can also be administered transdermally, anally or orally. The dosage units can be either liquid or solid. Typically, the dosage unit may be administered up to a maximum of about 4 times per day although a larger number of doses may be administered in certain cases.

The invention is further illustrated by the following examples, which are not to be construed in any way as imposing limitations upon the scope thereof. On the contrary, it is to be clearly understood that resort may be had to various other embodiments, modifications and equivalents thereof which, after reading the description herein, may suggest themselves to those skilled in the art without departing from the spirit of the present invention and/or the scope of the appended claims.

EXAMPLE I

Collagen Type II Induced Arthritis Model in DBA/IJ Mice

A model for investigating the autoimmunity in arthritis using collagen type II (CII) with complete Freund's adjuvant (CFA) to induce inflammatory arthritis in murine animals was initially reported by Trentham, et al., (See Trentham, D. E. et al., "Autoimmunity to type II collagen: an experimental model of arthritis", *J. Exp. Med.*, Vol. 146, pp. 857–868, 1977). Other types of collagen, as well as injecting the collagen with Freund's adjuvant, complete or incomplete did not induce polyarthritis. Daily clinical examination of the animals established the time of onset of arthritis after injection with the CII-CFA as 14 to 60 days. In subsequent investigations using the DBA/IJ strain of inbred mice, similarly using the CII-CFA, the mice developed an inflammatory polyarthritis in 4 to 5 weeks. These studies also showed that in the absence of CFA or with any other type of collagen, the animals did not develop arthritis. The progression of the arthritic condition ultimately led to the locking of one or more limbs. Both humoral and cellular immune responses to collagen type II appear to be involved in arthritic induction. The immune system has been shown to play a critical role in the disease progression. Autoimmunity to proteins normally found in the joint, such as collagen type II, has been observed in this arthritic animal model.

DBA/IJ mice were obtained from Jackson Laboratory, Bar Harbor, Maine. The mice were 7 to 10 weeks old. The mice were maintained in groups of two or three in polycarbonate cages. The mice were fed standard laboratory chow and were given water ad libitum. The collagen type II used in these studies was prepared as previously described in Trentham, et al. A pilot study was performed to show that the CII would induce arthritis before it was used in the controlled study. The mice were injected intradermally at the base of the tail with 0.1 ml containing 100 μg of CII emulsified in an equal volume of CFA. An identical booster was give 15 days later. Mice were examined daily for signs of swelling of the limbs as described previously. Arthritis was considered to be fully manifested when the animal had one limb locked (unable to bend at the joint). This usually occurred between 30 to 35 days after the initial CII injection.

Five days prior to the initial collagen injection, four treatment groups of 8 mice each were established:

saline control group

Mice treated with dimethylglycine (DMG)

Mice treated with Perna*

RNA polymerase

[*Perna is a potential anti-inflammatory agent made from New Zealand limpet.]

Each mouse was given a daily subcutaneous injection of 0.1 ml of the respective test drugs throughout the study. When the saline control mice developed arthritis, the study was terminated, except for 14 mice with locked limbs, which were then treated and observed for reversal of symptoms.

For the reversal study two treatment groups of seven mice each were given daily 0.1 ml subcutaneous injections of either saline control or RNA polymerase. The RNA polymerase for this study was prepared by using a concentration of 0.4 units (0.15 μg) of enzyme per dose. The enzyme concentrate was first inactivated in 0.4% phenol saline for 4 hours, then diluted with sterile saline for injection. The control saline was similarly treated. Blood samples from the retro-orbital sinus of the mice were taken at weekly intervals. The serum was collected and stored frozen at −20° C. for antibody assays to be performed at a later time. The dose of DMG was 100 μg/kg body weight and the dose of Perna was 1.3 g/kg body weight.

Figure 1:
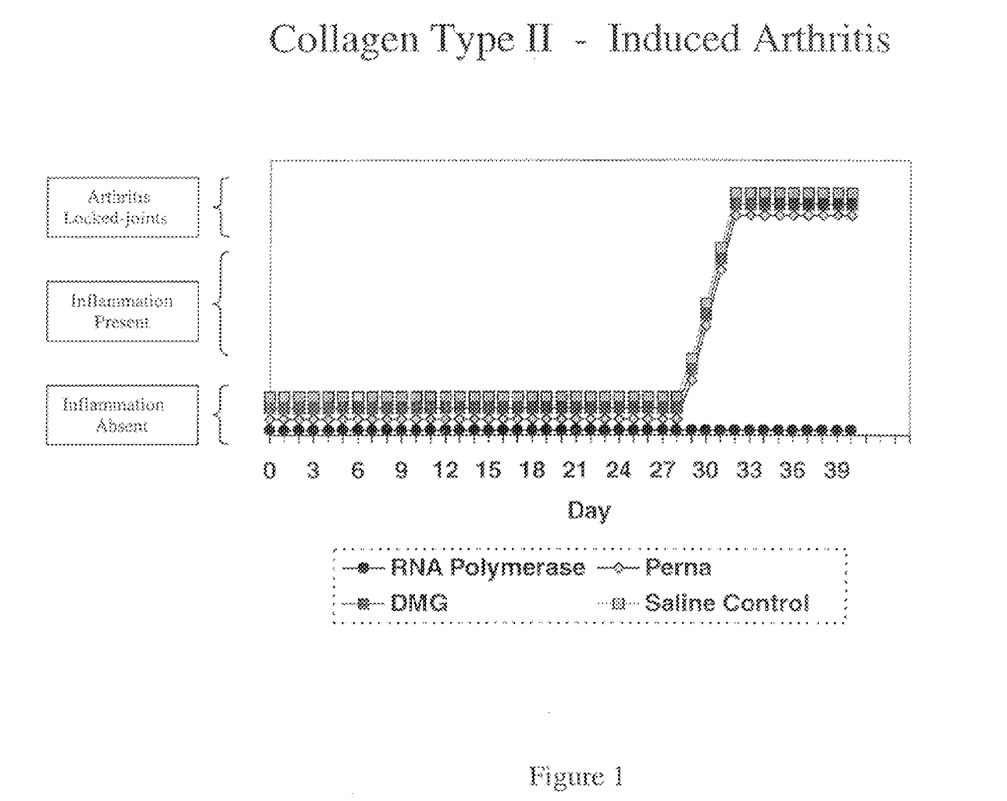
FIG. 1 is a graphical representation of the response of DBA/IJ mice to immunization with collagen II.

An initial inflammatory response, followed by a rheumatoid arthritic-like condition (locked joints), was observed in the saline control group, the DMG group and the Perna group. The group treated with the RNA polymerase did not elicit an inflammatory response nor an arthritic condition. (FIG. 1).

Figure 2:
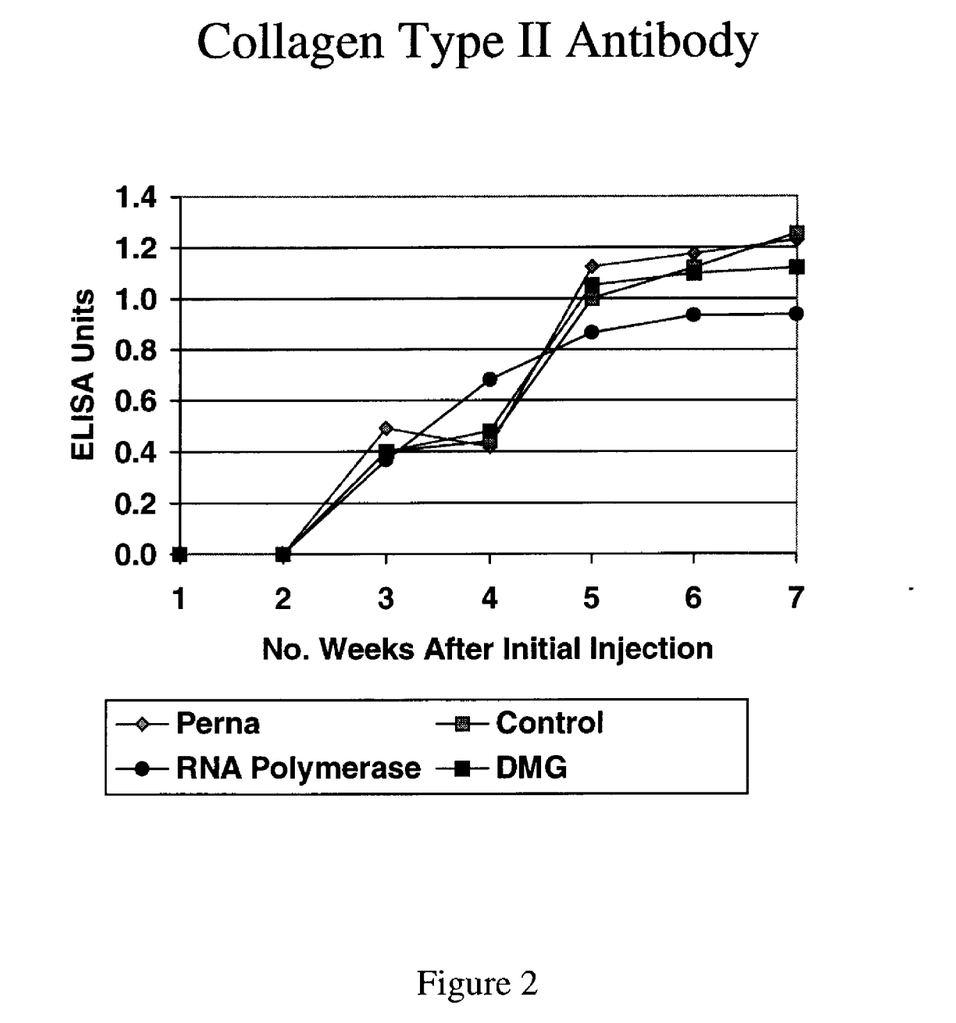
FIG. 2 is a graphical representation of the antibody response of DBA/IJ mice to immunization with collagen II.
Figure 3:
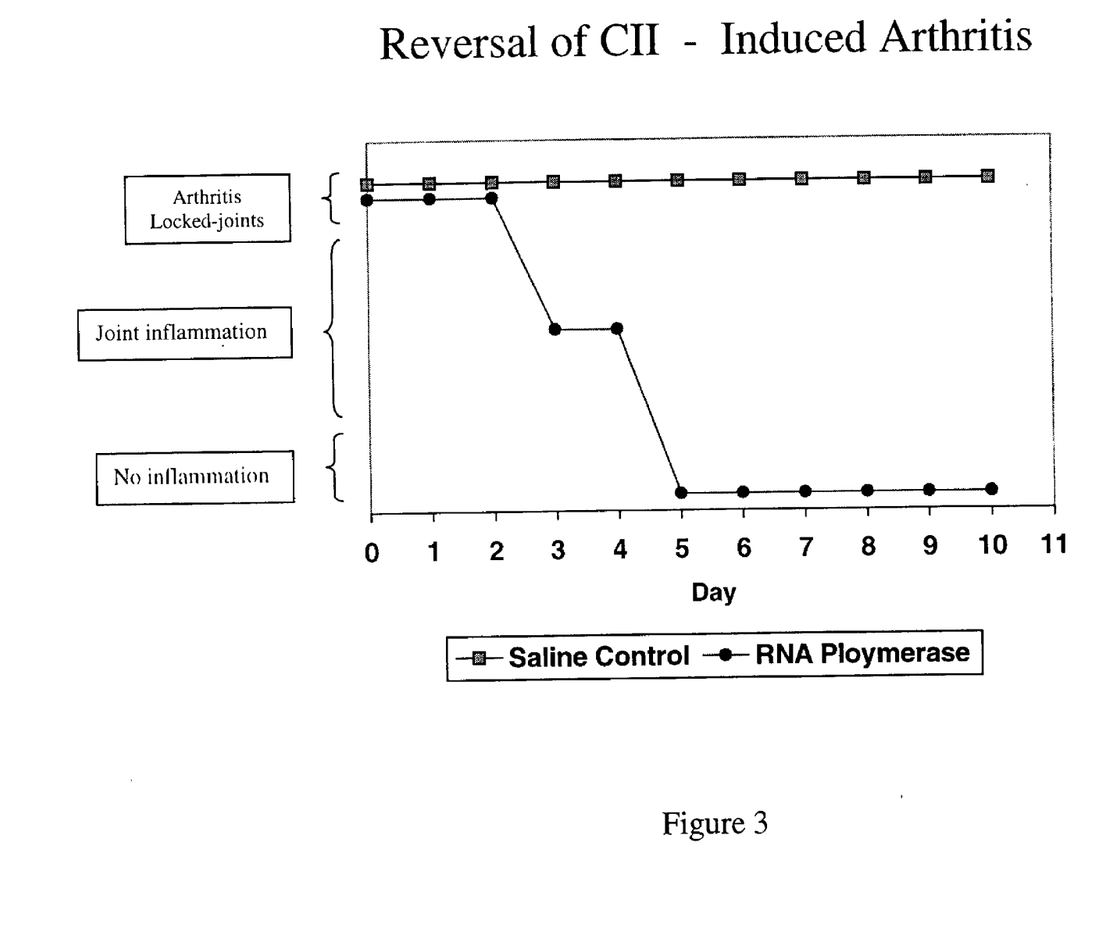
FIG. 3 is a graphical representation of the response to various treatments of DBA/IJ mice that have locked joints in response to the administration of collagen II.

Antibodies to collagen type II were present in each test group. At the time arthritis was manifested, the titer of antibody to collagen type II in the saline, DMG, and Perna groups was abruptly higher, above the 1.1 ELISA units at which arthritis occurs (FIG. 2). The non-arthritic group treated with RNA polymerase did not have an abrupt increase in collagen type II antibody titer. The RNA polymerase group antibody titer did not rise above the 0.1 ELISA units considered to indicate arthritis, but gradually increased, then leveled off at a titer below the 1.1 ELISA unit level.

Daily administration of low levels of RNA polymerase to DBA/IJ mice that had developed arthritis, as a result of injection with CII, reduced the swelling and stiffness of the joints within three days. The animals were symptom-free within five days and remained symptom-free for the 10 day duration of the experiment. The mice that were treated with saline after developing arthritis did not have their symptoms reversed at ten days, after which the mice were sacrificed.

Seven saline control mice that had developed arthritis (locked joints) from collagen induction were collected from several experiments and treated with 0.4 units of RNA polymerase daily until symptoms subsided (5 days). Blood samples were taken at the beginning of RNA polymerase treatment and at 5 days. Rheumatoid factor was determined by ELISA assay. The results of this experiment are shown in Table I.

TABLE I

Effect of RNA Polymerase on Rheumatoid Factor (RF) Titer in Arthritic Mice

| Animal No. | RF Titers (ELISA Units) | | |
|---|---|---|---|
| | Locked Joints | Unlocked Joints | % Decrease |
| 1 | 0.687 | 0.546 | 21 |
| 2 | 1.107 | 0.898 | 19 |
| 3 | 0.735 | 0.470 | 36 |
| 4 | 0.680 | 0.532 | 22 |
| 5 | 0.747 | 0.598 | 20 |
| 6 | 0.672 | 0.556 | 17 |
| 7 | 1.050 | 0.605 | 42 |

EXAMPLE II

A 20 year old mixed breed gelding with chronic foundering for the previous 10 years was treated with a single administration per day of 0.4 units of RNA polymerase subcutaneously in the neck for six days. The RNA polymerase for this study was prepared by using a concentration of 0.4 units (0.15 μg) of enzyme per dose. The enzyme concentrate was first inactivated in 0.4% phenol saline for 4 hours, then diluted with sterile saline for injection. All RNA polymerase preparations in Examples I through XVI were similarly prepared.

The owner continued to feed the horse excessively. The animal showed significant improvement after three days of treatment and was symptom-free within 6 days. The horse continues to be symptom-free until the present, a period of four months.

EXAMPLE III

A 12 year old Morgan mare was diagnosed by x-ray to have spavin in the hock (arthritis). The horse was treated with a daily subcutaneous administration of 0.4 units of RNA polymerase for six days. The horse showed dramatic improvement within six days and had no symptoms of arthritis for the next five months.

EXAMPLE IV

An 18 year old mare had severely limited vision, no hair around its eyes and the area around the eyes was heavily pigmented. The horse was diagnosed with autoimmune retinopathy (Vogt-Koyanagi-Harada syndrome) and was treated subcutaneously in the neck with a single dose of 0.4 units of RNA polymerase subcutaneously per day. After six days of treatment, the horse's vision had improved, the pigment around the eyes began to reappear and hair around the eyes was restored. The horse's condition continues to be normal two and one-half months after treatment.

EXAMPLE V

A 10 year old mare with severe foundering, as well as autoimmune retinopathy (Vogt-Koyanagi-Harada syndrome) characterized by hair loss around the eyes and loss of pigment around the eye, was treated with a daily subcutaneous dose in the neck of 0.4 units of RNA polymerase. The horse reversed its foundering and retinopathy tendencies within six days.

EXAMPLE VI

A 9 year old gelding quarter horse with a severe puncture wound in the hock causing extensive fluid discharge and inflammation as well as skin scarring was treated with a single subcutaneous administration in the neck per day for six consecutive days of 0.4 units of RNA polymerase. The horse responded very well to six days of treatment after which the horse was recovered from the abnormalities.

EXAMPLE VII

A 26 year old Appaloosa gelding with a systemic lupus erythematosus (eyes swollen shut and foundering in all four feet which did not respond to treatments such as banamine and butadiazol) was treated with a single subcutaneous administration in the neck per day of 0.4 units of RNA polymerase for six consecutive days. The horse's swollen eyes and inflammation of the lamina was dramatically reduced with three days of treatment and after six days of treatment, the horse was nearly normal. The horse continued to improve and was symptom-free within one and one-half weeks. Five months later, the horse is still symptom-free.

EXAMPLE VIII

Two 8 week old puppies with Staphylococcus induced pyodermas (swelling remaining after Staphylococcus infections were cured with lincomycin and cephalosporin) were treated with a single subcutaneous administration in the neck of 0.4 units of RNA polymerase per day for six consecutive days. The swelling was gone within three days and has not returned in either puppy.

EXAMPLE IX

A 12 week old German Shepherd with severe hip dysplasia which did not respond to steroid therapy was treated with a single subcutaneous administration in the neck per day of 0.4 units of RNA polymerase for six consecutive days. After the six days of treatment, the dysplasia was gone and the dog continues to show no signs of hip dysplasia.

EXAMPLE X

A 3 year old quarter horse with severe laminitis was treated with a single subcutaneous administration in the neck per day of 0.4 units of RNA polymerase for eight days. The horse's inflammation of the lamina was dramatically reduced with the six days of treatment. After two more days of treatment, the horse's inflammation was completely cured. The horse is now racing again.

EXAMPLE XI

A 7 year old Thoroughbred with severe degenerative osselet disorder was treated with a single subcutaneous administration in the neck per day of 0.4 units of RNA polymerase per day for six days. The horse recovered completely and is now back racing.

EXAMPLE XII

A 25 year old female with lupus erythematosus was treated with a single subcutaneous administration per day for six consecutive days of 0.4 units of RNA polymerase. After three days of treatment, the woman showed marked lessening of joint pain, lessening of the extreme fatigue associated with lupus, and decreased swelling of the membranes and tissue around the eyes. After six days of treatment, the patient exhibited no disease symptoms. The patient has remained symptom-free for several months.

EXAMPLE XIII

A 32 year old female with systemic lupus erythematosus was treated with twice daily sublingual doses of 0.4 units of RNA polymerase for seven consecutive days. She was free of disease symptoms after the seven days of treatment and has remained free of symptoms for over a year taking a sublingual dose of 0.4 units of RNA polymerase on an as needed basis at the earliest sign of a disease symptom.

EXAMPLE XIV

An eleven year old gelding quarter horse diagnosed as having probably a permanent stifle joint inflammation that was refractory to other treatments was treated with one month of daily 0.5 ml subcutaneous injections of 0.4 units of RNA polymerase from the T3 bacteriophage purchased from Pharmacia LKB Technologies (Piscataway, N.J.). The only drug the horse was given at the time was the T3 RNA polymerase. The horse put weight on the leg for the first time in 2 years, when the farrier shod it in March of 1992. As of December 1992, the horse was still doing very well and did not exhibit any symptoms of the former stifle joint inflammation.

EXAMPLE XV

An eight year old German Shepherd with hip dysplasia was treated with a 0.5 ml dose of 0.4 units of T3 RNA polymerase (Pharmacia LKB Technologies, Piscataway, N.J.) After six consecutive daily treatments, the animal's condition was greatly improved. The animal has remained symptom free.

EXAMPLE XVI

A twenty-five year old gelding with severe arthritis of the spine that did not respond to steroid or other therapies was treated with a 0.5 ml dose of 0.4 units of T3 RNA polymerase (Pharmacia LKB Technologies, Piscataway, N.J.) After six daily subcutaneous injections of the drug, the horse's coordination and ability to move were much improved.

It should be understood, of course, that the foregoing relates only to preferred embodiments of the present invention and that numerous modifications or alterations may be made therein without departing from the spirit and scope of the invention as set forth in the appended claims.

I claim:

1. A method for treating an inflammatory autoimmune dysfunction disorder in a human or animal comprising the step of administering to the human or animal a therapeutically effective amount of RNA polymerase, wherein the therapeutically effective amount of RNA polymerase is between $10^{-2}$ and $10^{-8}$ mg.

2. The method of claim 1, wherein the RNA polymerase is administered at periodic intervals.

3. The method of claim 1, wherein the RNA polymerase is administered by subcutaneous injection.

4. The method of claim 1, wherein the RNA polymerase is administered sublingually.

5. The method of claim 1, wherein the RNA polymerase is inactivated.

6. The method of claim 1, wherein the immune dysfunction disorder is selected from the group consisting of arthritis, laminitis, Vogt-Koyanagi-Harada syndrome, inflammation, lupus erythmatosus, pyodermas, hip displasia, osselet disorder, multiple sclerosis and myositis.

7. The method of claim 1, wherein the immune dysfunction disorder is lupus erythmatosus.

8. The method of claim 1, wherein the immune dysfunction disorder is arthritis.

9. The method of claim 1, wherein the immune dysfunction disorder is multiple sclerosis.

10. The method of claim 1, wherein the immune dysfunction disorder is Vogt-Koyanagi-Harada syndrome.

11. The method of claim 1, wherein between approximately 0.1 to 10 units of RNA polymerase is administered to the human or animal.

12. The method of claim 1, wherein the therapeutically effective amount of RNA polymerase is between $10^{-3}$ and $10^{-7}$ mg.

13. The method of claim 1, wherein the therapeutically effective amount of RNA polymerase is between $10^{-3}$ and $10^{-4}$ mg, and wherein the RNA polymerase has a specific activity of between 0.04 to 100 units of activity.

14. A method for treating multiple sclerosis in a human or animal comprising administering to the human or animal a therapeutically effective amount of RNA polymerase, wherein the therapeutically effective amount of RNA polymerase is between $10^{-2}$ and $10^{-8}$ mg.

15. The method of claim 14, wherein the therapeutically effective amount of RNA polymerase is between $10^{-3}$ and $10^{-7}$ mg.

16. The method of claim 14, wherein the therapeutically effective amount of RNA polymerase is between $10^{-3}$ and $10^{-4}$ mg, and wherein the RNA polymerase has a specific activity of between 0.04 to 100 units of activity.

17. The method of claim 14, wherein the RNA polymerase is inactivated.

18. The method of claim 14, wherein between approximately 0.1 to 10 units of RNA polymerase is administered to the human or animal.

19. The method of claim 14, wherein the RNA polymerase is administered at periodic intervals.

20. The method of claim 14, wherein the RNA polymerase is administered sublingually or by subcutaneous injection.

* * * * *